US011918747B2

(12) United States Patent
Moore et al.

(10) Patent No.: US 11,918,747 B2
(45) Date of Patent: Mar. 5, 2024

(54) BIOBURDEN REDUCTION SURGICAL MASKS/RESPIRATORS WITH USE IN PROTECTION AGAINST SARS-COV-2 INFECTIONS

(71) Applicants: Cullen Thomas Moore, Newtown, CT (US); Timothy S. Moore, Newtown, CT (US)

(72) Inventors: Cullen Thomas Moore, Newtown, CT (US); Timothy S. Moore, Newtown, CT (US)

( * ) Notice: Subject to any disclaimer, the term of this patent is extended or adjusted under 35 U.S.C. 154(b) by 229 days.

(21) Appl. No.: 16/940,313

(22) Filed: Jul. 27, 2020

(65) Prior Publication Data

US 2022/0023577 A1 Jan. 27, 2022

(51) Int. Cl.
| | |
|---|---|
| *A61M 16/10* | (2006.01) |
| *A41D 13/11* | (2006.01) |
| *A62B 18/02* | (2006.01) |
| *A62B 23/02* | (2006.01) |
| *H01F 7/02* | (2006.01) |

(52) U.S. Cl.
CPC ....... *A61M 16/105* (2013.01); *A41D 13/1161* (2013.01); *A62B 18/025* (2013.01); *A62B 23/02* (2013.01); *A62B 23/025* (2013.01); *A61M 2205/7509* (2013.01); *H01F 7/02* (2013.01)

(58) Field of Classification Search
CPC ................ A41D 13/11; A41D 13/1107; A41D 13/1123; A41D 13/1138; A41D 13/1146; A41D 13/1161; A41D 13/1192; A41D 13/1176; A61M 16/06; A61M 16/0605; A61M 16/105; A61M 2205/75; A61M 1/784; A62B 18/00; A62B 18/025; A62B 18/08; A62B 23/02; A62B 23/025; A62B 18/04; A62B 7/10; A61L 2101/26
See application file for complete search history.

(56) References Cited

U.S. PATENT DOCUMENTS

| | | | | | |
|---|---|---|---|---|---|
| 2,517,209 | A | * | 8/1950 | Jackson | A62B 21/00 422/120 |
| 4,414,973 | A | * | 11/1983 | Matheson | A62B 18/00 128/206.15 |
| 5,496,507 | A | * | 3/1996 | Angadjivand | B01D 39/08 264/423 |
| 6,102,040 | A | * | 8/2000 | Tayebi | A41D 13/1115 128/205.27 |
| 6,153,059 | A | * | 11/2000 | Wadsworth | B01D 39/1615 204/164 |
| 6,298,849 | B1 | * | 10/2001 | Scholey | A62B 9/04 128/205.27 |

(Continued)

FOREIGN PATENT DOCUMENTS

CN 203986231 U * 12/2014 ............. A41D 13/11

OTHER PUBLICATIONS

Zhai et al., Scalable-manufactured randomized glass-polymer hybrid metamaterial for daytime radiative cooling, Science Mar. 10, 2017, 377(6329) 1062-1066) (Year: 2017).*

(Continued)

*Primary Examiner* — Ophelia A Hawthorne
*Assistant Examiner* — Michael Milo

(57) ABSTRACT

The present invention in an embodiment relates generally to mask/respirator having a filter assembly detachable therefrom.

10 Claims, 4 Drawing Sheets

(56) References Cited

U.S. PATENT DOCUMENTS

| | | | | |
|---|---|---|---|---|
| 6,428,610 | B1* | 8/2002 | Tsai | B01D 39/163 |
| | | | | 264/151 |
| 6,701,925 | B1* | 3/2004 | Resnick | A62B 17/04 |
| | | | | 128/205.27 |
| 8,118,026 | B2* | 2/2012 | Gebrewold | A62B 23/025 |
| | | | | 128/206.17 |
| 9,247,775 | B2* | 2/2016 | Suzuki | A41D 13/1161 |
| 10,905,790 | B1 | 2/2021 | Moore et al. | |
| 2005/0133036 | A1* | 6/2005 | Steindorf | A41D 13/11 |
| | | | | 128/206.13 |
| 2008/0264413 | A1* | 10/2008 | Doherty | A61M 39/1011 |
| | | | | 128/202.27 |
| 2016/0332008 | A1* | 11/2016 | McAndrews | A62B 18/084 |
| 2018/0008848 | A1* | 1/2018 | Moulton | A41D 13/11 |
| 2019/0069611 | A1* | 3/2019 | Potnis | A41D 13/0053 |
| 2020/0114178 | A1* | 4/2020 | Waterford | A62B 23/025 |
| 2021/0154610 | A1* | 5/2021 | Carredo | A62B 23/02 |
| 2021/0268319 | A1* | 9/2021 | Liu | A62B 23/02 |

OTHER PUBLICATIONS

UltraTech (Ultra-X-Tex, Feb. 2020; https://irpltd.com/wp-content/uploads/2020/02/34P.pdf) (Year: 2020).*

Byrne JD, et al, Injection Molded Autoclavable, Scalable, Conformable (iMASC) System of Aerosol-based protection: A Prospective Singe-Arm Feasibility Study, BMJ Open 2020, 10:e039129 (Jul. 25, 2020).

Liverman CT, Yost OC, Rogers BME, et al., National Academies of Sciences, Engineering, and Medicine, Health and Medicine Division, Board on Health Sciences Policy, Committee on the Use of Elastomeric Respirators in Health Care. Reusable Elastomeric Tespirators in Health Care: Considerations for Routine and Surge Use, Washington (DC), National Academies Press (US); Dec. 6, 2018.

Lore et al., Effectiveness of Three Decontamination Treatments against Influenza Virus Applied to Filtering Facepiece Respirators, Ann. Occup. Hyg. 2012: Jan. 56(1)92-101.

Lindsley et al., Effects of Ultriviolet Germicidal Irradiation (UVGI) on N95 Respirator Filtration Performance and Structural Integrity, J. Occup Environ Hyg. 2015; 12(8): 509-17.

Fischer et al., Assessment of N95 respirator decontamination and re-use for SARS-CoV-2, medRxiv preprint, Apr. 24, 2020.

Buanno et al., Far-UVC light (222 nm) efficiently and safely inactivates airborne human coronaviruses, Scientific Reports, Nature Research, 2020:10:10285.

Zhai et al., Scalable-manufactured randomized glass-polymer hybrid metamaterial for daytime radiative cooling, Science Mar. 10, 2017, 377(6329) 1062-1066).

Ashby, M.F., Evans, A.G., Fleck, N.A., Gibson, L.J. Hutchinson, J.W , and Wadley, H.N.G.; Metal Foams: A Design Guide: Copyright @ 2000 by Butterworth-Heineman; cover, copyright: 1-5, 24-26; USA.

ACS Newsroom. Copper foam as a highly efficient, durable filter for reusable masks and air cleaners, ACS, https://www.acs.org/content/acs/en/pressroom/newsrelease/2021/march.

ERG materials & aerospace, Why is Duocel® copper foam so special, http://ergaerospace.com/materials/duocel-copper-foam/#:~:text=Why%20is%20%Duocel%C2%AE%20copper.a%20true%20metal%20skeletal%20structure.&text=its%20purity%20is%20typically%20that.the%20entirety%20of%20the%20material, downloaded Apr. 30, 2021.

American Elements®, COVID-19 Status: American Elements is currently in full operations and sales engineers are available for orders, https://www.americanelements.com/copper-foam-7440-50-8, downloaded Apr. 30, 2021.

* cited by examiner

BIOBURDEN REDUCTION SURGICAL MASKS/RESPIRATORS WITH USE IN PROTECTION AGAINST SARS-COV-2 INFECTIONS

CROSS REFERENCE TO RELATED APPLICATIONS

The present application does not claim priority to any other pending patent application national or foreign.

TECHNICAL FIELD

The present invention in an embodiment relates surgical masks and respirators having both a reusable, easily decontaminated, mask body and filter assembly. Such surgical masks and respirators may be used to protect against infection with SARS-CoV-2, causative agent of COVID-19. There is also provided in an embodiment, a filter assembly designed to sealedly coact with an adapter on a polymeric mask and/or respirator, said filter assembly comprising a housing surrounding a through void, the void providing space for filter material in said housing. Such filter assembly allows for extemporaneous production of filter combinations that may be directed to the infectious agent which is to be protected against. In an embodiment the filter assembly allows for magnetic coupling between the filter assembly and the polymeric mask and/or respirator body. In an embodiment there is also provided masks and respirators having both a reusable, easily decontaminated, mask body and filter assembly wherein the mask body and filter assembly may be decontaminated by different methods. In one embodiment, the mask body is manufactured from one or more substantially translucent polymeric layer(s) comprising SiO2 microspheres of about 1 um-10 um in diameter, more preferably about 3 um-9 um in diameter, 5 um-8 um in diameter, and yet more preferably about 8 um in diameter, with a metallic backing, e.g. silver, adjacent one face of a layer or multiple layer. Such body provides a cooling effect when impinged by infrared wavelengths, particularly those between 8 and 13 um, to which they wearer may be exposed, such as in the external environment or in regard to certain surgical lights.

BACKGROUND

A new coronavirus, designated SARS-CoV-2, has ravaged the world since 2019. This virus first jumped into humans in Wahun, Hubei Province, China, and then quickly spread across the world. COVID-19 represents a global public health concern and WHO has declared it a public health emergency. SARS-CoV-2 rapidly increased in spread in an epidemic scale since its first appearance in Wuhan, China, around December 2019. On Jan. 31, 2020, the Secretary of HHS issued a declaration of public health emergency related to COVID-19.

The FDA has recognized that decontamination systems play an important role in the ongoing efforts to help address the shortages of surgical masks/respirators during COVID-19 (See, May 2020 Guidance for Industry and Food and Drug Administration Staff in "Recommendations for Sponsors Requesting EUAs for Decontamination and Bioburden Reduction Systems for Surgical Masks/Respirators During the Coronavirus Disease 2019 (COVID-19) Public Health Emergency). In particular the FDA has recognized that the need for surgical masks/respirators may outpace the supply available to healthcare organizations during the COVID-19 public health emergency. It has also recognized that multiuse of surgical masks/respirators will dramatically decrease the bioburden associated with single-use masks. Therefore, the FDA has expressed interest in interacting with others about systems that may be effective at decontaminating or reducing the bioburden of otherwise single-use, disposable surgical masks/respirators.

The FDA regulates the distribution of face masks and respirators for medical purposes. Typically there are two primary avenues for manufacturers of such devices to receive FDA approval—approval through the premarket approval (PMA) process or via the FDA 510k process. To advance through the 510K process one must demonstrate that the new device is substantially equivalent to an existing legally market device in terms of technological characteristics such that it does not raise different questions of safety and effectiveness of the predicate device. The FDA processes 510K submissions in 30-90 days. A PMA requires that one prove a new device is safe and effective for the end user and typically requires clinical trials with human participants along with laboratory testing. The FDA has 180 days to accept or reject such a PMA application.

In its Guidance, the FDA provides an Emergency Use Authorization ("EUA") process to allow for use of new surgical masks and respirators intended for a medical purpose during COVID-19. The FDA is interested in interacting with sponsors about systems that may reduce the bioburden of otherwise single-use, disposable surgical masks and respirators, and has stated that it will issue an EUA when certain criteria for issuance are met. The reduction of bioburden of N95 respirators for single use users in conjunction with existing CDC Reuse recommendations is one such tier available for an EUA.

Coronavirus particles are spherical in nature and have a diameter of approximately 0.125 microns, with the smallest particles being about 0.06 microns and the largest about 0.14 microns. From a filtration point of view, it is the droplet that must be removed from the air, and these range from 0.5 microns to approximately 15 microns, with most in the lower range. Coronaviruses are enveloped positive-sense RNA viruses. Enveloped viruses have lipid membranes.

In a recent study by Byrne J D, et al, *Injection Molded Autoclavable, Scalable, Conformable (iMASC) System of Aerosol-based protection: A Prospective Singe-Arm Feasibility Study*, BMJ Open 2020, 10:e039129 (Jul. 25, 2020) a new reusable, sterilizable N95 filtering facepiece respirator ("FFR") developed in a joint project between MIT and Harvard University researchers. The mask is described as being constructed of liquid silicone rubber ("LSR") "said to be used due its conformable capacity, sterilisability through multiple methods, and compatibility with injection mounding for fabrication scalability." The filters are described as "dual, replaceable filters" of N95 material "that can be inserted and replaced as needed." It is said that "[a] single regular N95 generated up to five filters for the iMASC system, thus extending the N95 material use.

The concept of a reusable respirators is said in the Byrne article to be set forth in a 2018 consensus report by the National Academies of Engineering, Science and Medicine that such are desirable for stockpiling for emergencies (National Academies of Sciences, Engineering, and Medicine, Health and Medicine Division, Board on Health Sciences Policy, Committee on the Use of Elastomeric Respirators in Health Care. *Reusable elastomeric respirators in health care: Considerations for routine and surge use*, Washington (DC), National Academies Press (US), 2018).

The present inventor has noted several deficiencies in the iMASC configuration. First, it is noted that the filters are removed after use evidently by pushing them out from the front exterior side of the masks (as shown in figures the filters are installed through the face side of the mask). Such manipulation would require considerable dexterity in removing the filters with mask being held along surfaces where contamination could exist (particularly the front of the mask). Second the placement of the filters must be done exactingly as there is the possibility of leakage if the filters are not put in correctly. Third the filters are designed to be discarded with each use. The discarding of the filters leads to more bioburden than would be desired, and would require safety procedures in the disposal of the same. The indication in the article that only five filters could be generated from "a single regular N95 FFR for the IMASC mask also suggests that the bioburden would still be high. Fourth, the polymer used to make the body of the mask is not ideal in being affected by autoclaving and isopropanol alcohol soak: "We found that 10 autoclave cycles make the mask slightly stiffer . . . and the isopropanol alcohol, soak makes the material less stiff." Further the IMASC mask was not found to be preferable over a N95 FFR by 75% of the participants surveyed.

The present inventor sets forth in embodiments a reusable surgical mask and respirator that can be used to treat COVID-19 patients, that allows for easy coupling and decoupling of the filter from the polymeric body, that allows the filter material as well as the mask/respirator body to be decontaminated and reused multiple times, with different decontamination techniques being able to be applied to mask and filter milter, that employs a polymeric body that allows for easy decontamination without effect on the body integrity, and that optionally provides a polymeric body that provides cooling to the wearer when the wearer is exposed to wavelengths of 0.3 um to 25 um, and particularly to 8 to 13 um.

SUMMARY OF THE INVENTION

Accordingly, the invention herein provides in an embodiment surgical masks and respirators having both a reusable, easily decontaminated, mask body and filter assembly. Such surgical masks and respirators may be used to protect against infection with SARS-CoV-2, causative agent of COVID-19. There is also provided in an embodiment, a filter assembly designed to sealedly coact with an adapter on a polymeric mask and/or respirator, said filter assembly comprising a housing encompassing a void for placing one or more filter material into said housing. Such filter assembly allows for extemporaneous production of filter combinations that may be directed to the infectious agent which is to be protected against when filters of different fabrication dimensioned to sealedly fit within the void are provided. In an embodiment the filter assembly allows for magnetic coupling between the filter assembly and the polymeric mask and/or respirator body. In an embodiment there is also provides masks and respirators having both a reusable, easily decontaminated, mask body and filter assembly, the mask body being manufactured from one or more substantially translucent polymeric layer(s) comprising $SiO_2$ microspheres of about 1 um-10 um in diameter, more preferably about 3 um-8 um in diameter or 5 um-8 um in diameter, and yet more preferably about 8 um in diameter, with a metallic backing, particularly silver, adjacent the face. Such body provides a cooling effect when impinged by infrared wavelengths, particularly those between 8 and 13 um, to which they wearer may be exposed, such as in the external environment or in regard to certain surgical lights. The polymer layer(s) may preferably be at least one of polyethylene, poly(methyl methacrylate) or polymethylpentene. There is also provided in an embodiment, a polymeric mask and/or respirator allowing for magnetic coupling between the filter assembly and the polymeric mask and/or respirator body.

DESCRIPTION OF SPECIFIC EMBODIMENTS

Figure 1:
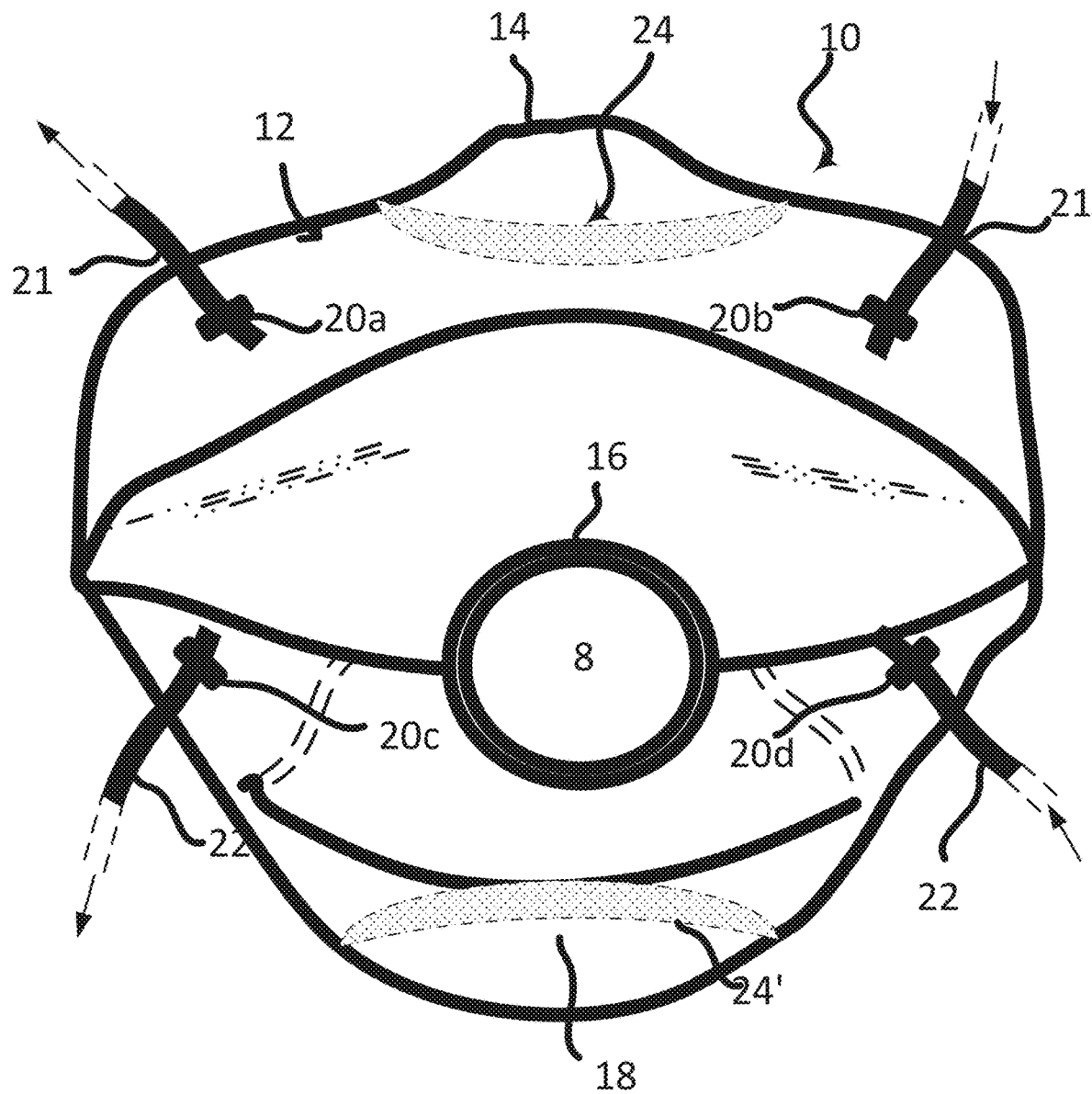
FIG. 1 is frontal view of a mask/respirator embodiment with dotted structure found on the opposing (back) side of the mask/respirator.

In one embodiment there is provided a respirator for use in the treatment of medical patients comprising: (a) a mask body having a void therein and a coupling surrounding the oid; (b) a harness comprising one or more straps that are joined to the mask body on opposing sides thereof; (c) a detachable filter assembly comprising a sidewall housing encompassing a void dimensioned for receipt of one or more filters, the detachable filter assembly having a coacter to coact with said coupling of the mask body; such that when the coacter of said filter assembly coasts with said mask body coupling the void in the mask body is sealed. The void is optimally positioned and dimensioned to permit breath from the wearer of said respirator, and air outside of said respirator, to be exchanged. The coupling on the mask body may be selected, for example, from the group comprising: magnetic material, magnetically attractable material, threads, deformable flange(s). In the case that the coupling of the mask body is magnetic material, the coacter of the detachable filter preferably is a magnetically attractable material or a magnetic material. When the coupling of said mask body is a magnetically attractable material, preferably the coacter of the detachable filter is magnetic material When the coupling of the mask body is thread, the coacter of the filter assembly preferably is counter thread. When the mask body coupling is deformable flange(s), preferably the coacter of the detachable filter assembly is dimensioned to be sealedly held by the flanges of said mask body. Preferably the filter assembly can be easily inserted into the flange(s) and then easily released by the flanges by adding pressure to the outside of the filter assembly. Filters that may be used in the filter assembly include lipophilic filters, electrostatic non-woven polypropylene fiber, hydrophilic filters, antimicrobial filters etc. The filter assembly may comprise filters directed to SARS-CoV-2. The harness straps are preferably elastic. The respirator may further comprise on the on the side designed for facing the face opposing grasping straps to permit one grab such straps to allow for easier removal when said filter assembly is positioned on the front of said mask.

In another embodiment, there is disclosed a mask comprising: (a) a polymeric mask body encompassing therein breathe-through filter material; (b) a harness joined to the mask body on opposing sides thereof; wherein the polymeric mask body is composed of a metamaterial comprising randomly distributed silicon dioxide microspheres mixed in a transparent polymer layer which is affixed to a metal layer on one surface of the polymer layer; and wherein the breathe-through filter material is positioned and configured in the polymeric mask to allow for air from the mouth and nose of the wearer of such mask to be filtered through such material. The mask transparent polymer layer is preferably selected from at least one of the group: poly(methyl methacrylate), polyethylene and polymethylpentene. Particularly polymethylpentene is 3D printable, allowing for masks to be made that conform to individual faces. The metal layer is preferably silver. The breathe-through filter material may be selected from at least one of cloth, electrostatic non-woven polypropylene fiber, polypropylene, polybenzimidazole nanofiber, cellulose, activated carbon, and thin glass fibers, as well as other known filter materials.

Also disclosed in an embodiment is a respirator filter assembly configured for coupling to a respirator about a void in the respirator body to seal said void, the assembly comprising: (a) a sidewall housing encompassing a through void; (b) a first filter comprising copper foam sealedly positioned in said side wall housing; (c) a second filter comprising electrostatic non-woven polypropylene fiber positioned tandem to said first filter. Preferably the first filter has higher average porosity than the second filter. The respirator filter assembly of sidewall housing may be fabricated from copper. In one embodiment, the respirator filter assembly magnetically couples to structure about said void of said respirator body. The respirator filter assembly may further comprising a third filter comprising lipophilic material. Multiple filters may be positioned in the filter assembly depending on size of filter assembly and the corresponding width of the filters.

Figure 2:
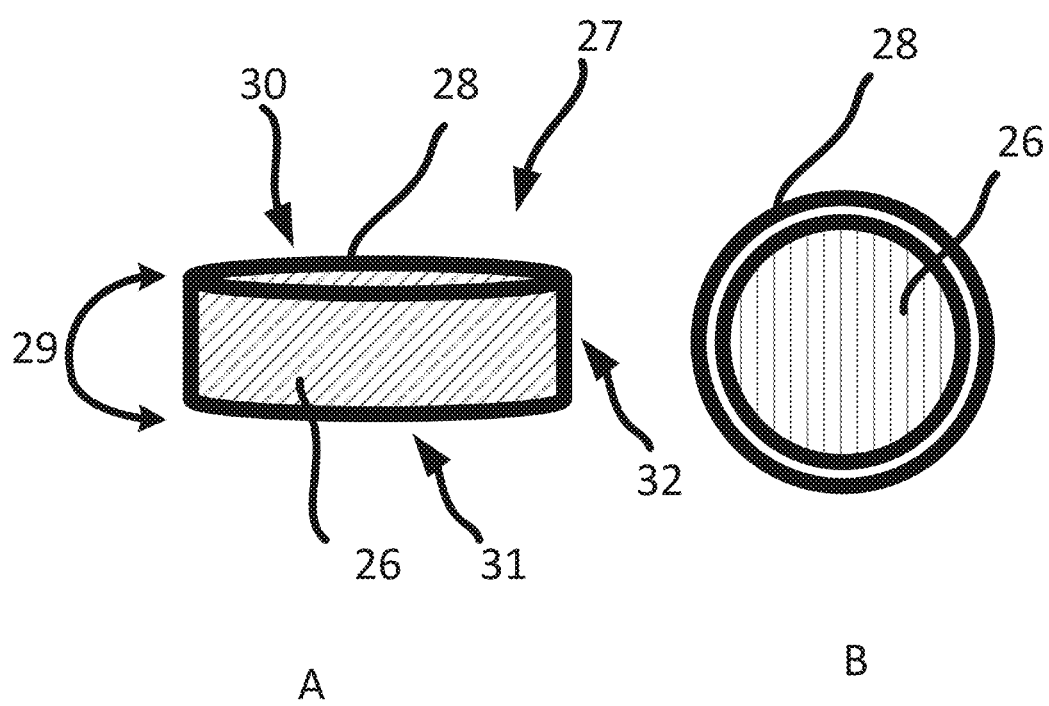
FIG. 2 is embodiment side view (A) of filter housing and top view (B) of a filter assembly with filter material enclosed in filter housing (A).

FIG. 1 illustrates a frontal view of an embodiment mask respirator 10 embodiment with dotted structure (24, 24') found on the opposing (back) side of the mask/respirator. Mask/respirator 10 comprises a polymeric body 12 with a coupling 16 for filter assembly 27 (FIG. 2). Such coupling 16 surrounds a through void 8. Coupling 26 may comprise, for example, a magnetic material that is attracted to metal found on a surface of filter assembly 27 (FIG. 2), a metal which is magnetically attractable to a magnetic material found on a surface of filter assembly 27 (FIG. 2), screw threads designed for mating with threads found along the lateral side of filter assembly 27 (FIG. 2) (not shown in FIG. 2), a circumferential flange capable of receiving and sealingly coupling filter assembly 27 (FIG. 2). A portion of the polymeric body 12 is designed to have nose fitting portion 14 and mouth and chin fitting portion 18. Mask/respirator 10 attaches to head of user by way of upper strap 21, and lower strap 22. Upper strap 21 is affixed to polymeric body 12 by way of fixation 20a and 20b while lower strap 22 is affixed to polymeric body 12 by fixation 20c and 20d. Grabbing structure 24 and 24' are found on the other side of the mask (face directed portion), and provide for structure to hold the mask on the face side when the filter assembly 27 is removed. Grabbing structure 24 and 24' may be, for example, one or more elastomeric bands, one or more plastic strips, one or more cloth strips, or one or more metal strips (or combination thereof). Preferably grabbing structure 24 and 24' are positionally opposed as shown.

FIG. 2 illustrates a filter assembly 27. Filter assembly 27 contain filter material 26 is a sidewall housing 29 wherein the filter material courses from the top of the assembly 30 to the bottom of the assembly 31. In the illustrated embodiment, there is a band 28 which may comprise magnetic attracted metal, or magnetic material along on or both sides of filter assembly 27 that allows for coupling with mask portion 16 of FIG. 1. As stated above, filter assembly 27 may alternatively of in conjunction comprise a threaded surface (not shown) along its lateral surface 32 to allow for coupling with a counter threaded surface found in mask portion 18 of FIG. 1.

Figure 3:
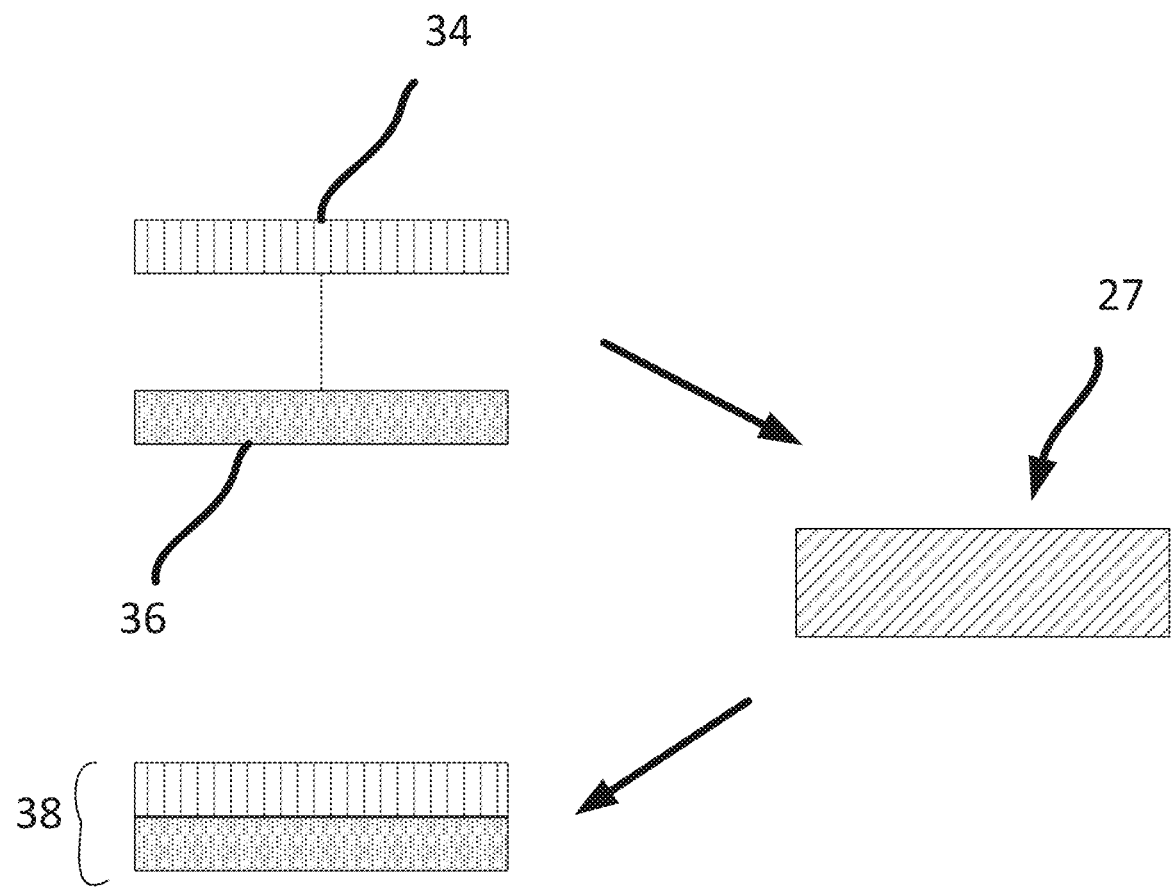
FIG. 3 is a depiction of a method for making a combination filter in the filter housing in an embodiment of the present invention.

FIG. 3 illustrates a depiction of a method for making a combination filter in the filter housing in an embodiment of the present invention. Multiple filters having different properties such as filters 34 and 36 are provided (side view shown). For example, coronaviruses are known to be enveloped viruses. Such viruses are encased within a lipid bilayer. Once an envelope of such a virus is lysed, the virus loses its functional receptors and is not able to infect susceptible cells. Thus, one of filters 34 and 36 can be a lipophilic filter which entraps lipophilic materials, for example, Ultra-X-Tex. The other filter may be made for example of polypropylene such as electrostatic non-woven polypropylene fiber found in N95, N99, and N100 (the last numbers providing percent efficiency in removal of particles, with N100 being 99.97 percent efficient, the same as a HEPA quality filter). Other filters may be appropriate such as copper foam with copper being known to be bacteriocidal and viricidal to certain bacteria, and viruses. Thus, the filter assembly allows the user of the mask to stack filters in a manner that is most appropriate to the infectious agent that is being treated. Such filters may be provided with instructions as to preferred assemblies for different infectious agents. Selection is made from among such filters for placement into the hollow (not shown) of filter assembly 27 (side view shown). The filters are placed into in juxtaposition as instructed for the particular disease state that will likely be encompassed to form a combination of filters as shown in cut view of 27. The order of filters may be specified to meet certain specifications, such as the filter with the largest pores being exposed to the incoming air before a filter with smaller pores.

Figure 4:
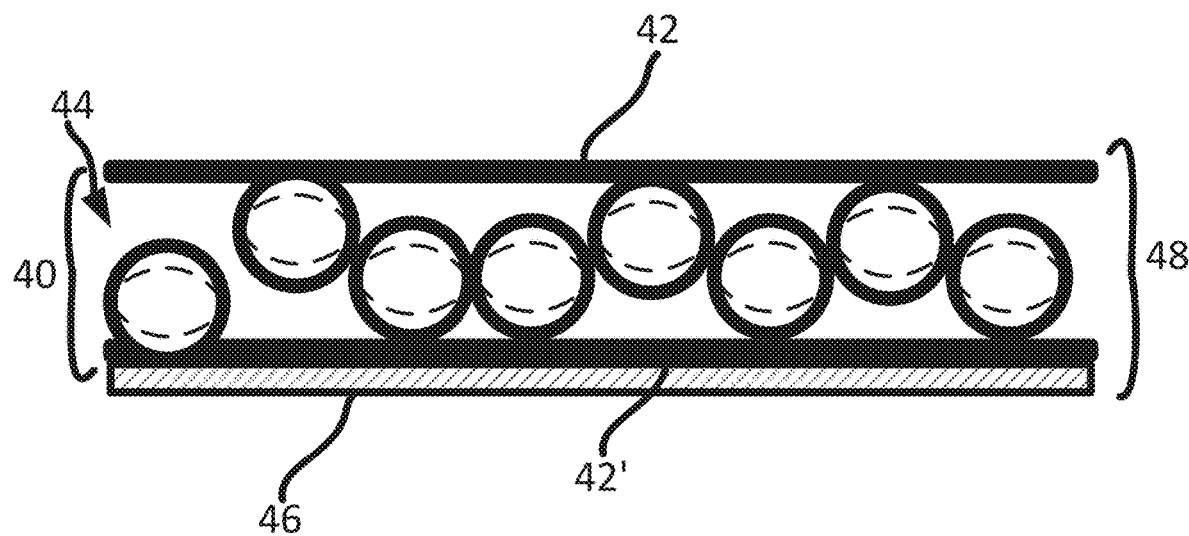
FIG. 4 is a side cut view of a glass sphere containing polymer with metal backing of the prior art that finds use an embodiment mask/respirator of the present invention.

FIG. 4 illustrates a polymeric material that may find use in the present invention. Metamaterial 48 is composed of a polymer 40, such as poly(methyl methacrylate), polyethylene and/or polymethylpentene, in which silicon dioxide ($SiO_2$) microspheres 44 are randomly distributed. A metallic layer 46, such as a silver layer, is in contact to one of the surfaces 42 or 42' of the silicon dioxide infused polymer 40. A mask or respirator of such material is fabricated such that the metallic layer 46 is adjacent the skin to provide cooling when the mask is exposed to wavelength in the atmospheric transmission window of 8 to 13 um.

The filter assemblies of the present invention proffer advantages over the filter systems of prior art masks/respirators. First, they allow for easy decoupling between the mask/respirator and the filter assembly. Removal of the filter assembly may be from the exterior side of the mask/respirator. The assembly may include a protrusion, such as a handle, a knob, a push button, coupled to the filter assembly that allows one to grasp the assembly from the front of the mask/respirator (not shown) or may be removed by way of use of a glove to grasp the assembly and remove it from the mask/respirator. The mask/respirator itself in an embodiment having grabbing structure 24 and 24' on the face directed surface of the mask allows one to grasp the mask from the face side (presumably the non-contaminated side) le the filter assembly 27 is removed.

Filter assembly 27 need not be disposed of as suggested in the prior art. Instead, such assembly may be disinfected and used again using appropriate procedures, such as cleaning with alcohol based liquids, autoclaving, or preferably by treatment with UV radiation.

UVC light is known to possess a very powerful germicidal effect not only on bacteria, but also viruses. It is believed that such radiation leads to pyrimidine dimers interfering with DNA and RNA replication and transcription. Typically such UVC irradiation has been performed using low-pressure mercury UV lamps which emit about a 254 nm peak wavelength (86 percent of light at around 254 nm.)

Before COVID-19, studies had shown that ultraviolet germicidal irradiation was able to reduce virus load by greater than 4 log median a tissue culture infective dose placed on a N95 filtering face piece respirator ("FFR"). Such reduction was also seen in regard to microwave-generated steam, and moist heat. See. Lore et al., *Effectiveness of three decontamination treatments against virus applied to filtering facepiece respirators*, Ann. Occup. Hyg. 2012: Jan: 56(1) 92-101. Lindsley et al., *Effects of Ulrtiviolet Germicidal Irradiation (UVGI) on N95 Respirator Filtration Performance and Structural Integrity*, J. Occup Environ Hyg. 2015; 12(8): 509-17 also found in testing 4 N95 masks/respirators that UV sterilization might be used on such masks/respirators to allow for reuse. Studies conducted by Fischer et al., *Assessment of N95 respirator decontamination and re-use for SARS-CoV-2*, medRxiv preprint, Apr. 24, 2020, https://doi.org/10.1101/2020.04.11.20062018, demonstrate that UV radiation of 260-285 nm for about 50 minutes could be used to decontaminate surgical respirators of SARS-CoV-2 for re-use up to three times. Recent research has shown that far-UVC light in the range of 207 to 222 nm can control the spread of airborne-mediated microbial disease without the need for more penetrating UVC wavelengths outside this range. See, Buanno et al., *Far-UVC light (222 nm) efficiently and safely inactivates airborne human coronaviruses*, Scientific Reports, Nature Research, 2020: 10:10285. Far-UVC light can also effectively be generated by filtered excimer lamps which are known to emit UV-C light from 172 nm to 310 nm. Buoanno et al. found in respect of the air alone it took approximately 25 minutes to inactivate 99.9 percent of human coronaviruses alpha HCV-229 E and beta HCoV-OC43, shorter than the time noted by Fischer et al. using higher wavelengths. The present inventor has understood that such lower UVC wavelengths of 207 to 222 nm can work as well on filter assemblies of masks/respirators that might be infected with SARS-CoV-2.

Thus the filter assembly can be cleaned in a manner different than the mask/respirator body. For example, a polymeric body can be cleaned using alcohol, a bleach solution or autoclaving as set forth by Byrne et al. On the other hand, the filter assembly may be cleaned effectively by UV radiation such that it structure is not adversely affected. The filter assemblies may be marked in a manner to match the filter assembly with the particular mask/respirator body, so both at returned to the same prior user. Reuse of the filter assembly greatly reduces the bioburden associated with use of surgical masks/respirators.

The polymer of said mask/respirator body may preferably be at least one of polyethylene, poly(methyl methacrylate) and polymethylpentene. No reduction in tensile strength may be noted when cleaned with alcohols as reported by Byrne et al. to be associated with the cleaning with isopropanol in respect of liquid silicone rubber. These polymers are known to work well when mixed with silicon dioxide microspheres and backed by a metal film, such as silver, to allow for reflection of solar irradiation (spectroscopic response spanning two orders of magnitude in wavelength form 0.3 um to 25 um with extreme emissive affect at 8 to 13 um (thermal IR)) (See, Zhai et al., *Scalable-manufactured randomized glass polymer hybrid metamaterial for daytime radiative cooling*, Science 10 Mar. 2017, 377(6329) 1062-1066)). Such glass-polymer metamaterial containing micrometer-sized $SiO_2$ spheres randomly may comprise polymethylene pentene which is transparent The present inventor has recognized that such material has not been used in masks/respirators but has the advantage of cooling surfaces that are exposed to solar irradiation when the metal surface is opposite the face. Furthermore the hybrid metamaterial can be made as thin as 50 um and still provide uniform and sufficiently strong absorbance across the entire atmospheric window resulting in broadband infrared emission for radiative cooling. Such material may also find use in certain surgery rooms where non-LED surgical lights are still used, and certainly in warm outside environments, in both cases enabling longer wear of the masks.

What is claimed is:

1. A respirator system comprising:
   (a) a mask body having a face-directed surface and an exterior-directed surface, a nose fitting portion and a mouth and chin fitting portion, the mask body having at least one mask void and a coupling surrounding each of said mask void(s);
   (b) a head harness comprising upper and lower straps that are joined to the mask body on opposing sides thereof configured for attachment of said mask body to a head of a person;
   (c) a detachable filter assembly consists of a monolithic sidewall housing fabricated from copper defining a sidewall through-void dimensioned for receipt of a plurality of unencapsulated filters, a coacter on an outer circumference of the sidewall housing to sealedly coact with said coupling of said mask body surrounding the mask void, and a multiplicity of unencapsulated filters consisting of filter material consisting of at least one copper foam filter, at least one lipophilic filter, and at least one non-woven polypropylene fiber filter, each unencapsulated filter dimensioned to sealedly-fit itself within said sidewall through-void of said detachable filter assembly and to allow a plurality of distinct filters to fit therein; wherein when said co-acter of said detachable filter assembly is configured to magnetically coact with said mask body coupling;
   wherein said mask void is positioned and dimensioned to permit breath from the wearer of said respirator system, and air outside of said respirator system, to be exchanged; and
   wherein said detachable filter assembly is configured to allow extemporaneous fabrication of combinations of said unencapsulated filters by a person within its sidewall through-void and removal of said unencapsulated filters.

2. The respirator of claim 1 wherein the coupling on said mask body is selected from the group comprising: magnetic material, and magnetically attractable material.

3. The respirator of claim 2 wherein the coacter of said detachable filter assembly is magnetically attractable material or a magnetic material when the coupling of said mask body is magnetic material.

4. The respirator of claim 2 wherein the coacter of said detachable filter assembly is magnetic material when the coupling of said mask body is magnetically attractable material.

5. The respirator system of claim 1 wherein the head harness is elastomeric.

6. A kit for contemporaneous manufacture of a mask for optimized filtration, the kit comprising:

(a) a mask body having a face-directed surface and an exterior-directed surface, a nose fitting portion and a mouth a chin fitting portion, said mask body having at least one mask void therein and a coupling surrounding said mask void, said mask body having a head harness comprising upper and lower straps that are joined to the mask body on opposing sides thereof configured for attachment of said mask body to the head of a person;

(b) a detachable filter assembly consists of a monolithic sidewall housing fabricated from copper defining a sidewall through-void dimensioned for receipt of at least two distinct unencapsulated filters, a coacter on an outer circumference of the sidewall housing to sealedly coact with said coupling of said mask body surrounding the said mask void, and a multiplicity of distinct unencapsulated filters consisting of filter material consisting of at least one copper foam filter, at least one lipophilic filter, and at least one non-woven polypropylene fiber filter, each distinct unencapsulated filter dimensioned to sealedly-fit itself within said sidewall through-void of said detachable filter assembly and to allow a plurality of distinct filters to fit therein, when said co-acter of said detachable filter assembly is configured to magnetically coact with said mask body coupling; (c)

(d) instructions indicating which of said plurality of distinct filters should be placed in said detachable filter assembly void depending on an organism or material sought to be filtered.

7. The kit of claim 6 wherein each of the plurality of distinct filters has a different average pore size.

8. The kit of claim 6 including at least three distinct-filters configured for positioning within the void of the detachable filter assembly.

9. The kit of claim 6 wherein the detachable filter assembly is capable of receiving at least three of the multiplicity of distinct filters.

10. A kit for contemporaneous manufacture of a mask for optimized filtration, the kit comprising:
  (a) a mask body having a face-directed surface and an exterior-directed surface, a nose fitting portion and a mouth a chin fitting portion, said mask body having at least one mask void therein, said mask body having; a head harness comprising upper and lower straps that are joined to the mask body on opposing sides thereof configured for attachment of said mask body to the head of a person;
  (b) a detachable filter assembly consists of a monolithic sidewall housing fabricated from copper defining a sidewall through-void, a coacter on an outer circumference of the sidewall housing to sealedly coact with a coupling of said mask body surrounding the mask void, and a plurality of distinct unencapsulated filters consisting of filter material consisting of at least one copper foam filter, at least one lipophilic filter, and at least one non-woven polypropylene fiber filter, each distinct unencapsulated filter dimensioned to sealedly-fit itself within said sidewall through-void of said detachable filter assembly and to allow a plurality of distinct filters to fit therein and removed therefrom, when said co-acter of said detachable filter assembly is configured to magnetically coact with said mask body coupling.

* * * * *